United States Patent [19]

Lo

[11] Patent Number: 4,908,228

[45] Date of Patent: Mar. 13, 1990

[54] DIOXOLANE, DIOL AND DIACRYLATE SILICON COMPOUNDS AND METHOD FOR THEIR PREPARATION AND USE

[75] Inventor: Peter Y. K. Lo, Midland, Mich.

[73] Assignee: Dow Corning Corporation, Midland, Mich.

[21] Appl. No.: 338,831

[22] Filed: Apr. 14, 1989

Related U.S. Application Data

[63] Continuation of Ser. No. 914,899, Oct. 3, 1986, abandoned.

[51] Int. Cl.$^4$ ............................................. B05D 3/06
[52] U.S. Cl. .................................. 427/54.1; 548/406; 549/214; 528/15; 528/26; 528/24; 528/27; 522/99; 522/148; 522/172; 525/479
[58] Field of Search ........................ 548/406; 549/214; 528/15, 26, 27, 24; 522/99, 148, 172; 427/54.1; 525/479

[56] References Cited

U.S. PATENT DOCUMENTS

| | | | |
|---|---|---|---|
| 4,210,596 | 7/1980 | Cella | 528/34 |
| 4,331,704 | 5/1982 | Watson, Jr. et al. | 522/97 |
| 4,431,789 | 2/1984 | Okazaki et al. | 525/479 |

Primary Examiner—Melvyn I. Marquis
Attorney, Agent, or Firm—George A. Grindahl

[57] ABSTRACT

Dioxolane-substituted silicon compounds are prepared by a hydrosilylation reaction between a silicon hydride and an aliphatically unsaturated dioxolane compound. The dioxolane-substituted silicon compounds are thereafter converted to diol-substituted silicon compounds and then to diacrylate-substituted silicon compounds. The latter are useful in a curable coating composition for providing a substrate with an adhesive-releasing coating.

30 Claims, No Drawings

DIOXOLANE, DIOL AND DIACRYLATE SILICON COMPOUNDS AND METHOD FOR THEIR PREPARATION AND USE

This is a continuation of co-pending application Ser. No. 914,899 filed on Oct. 3, 1986, and now abandoned.

BACKGROUND OF THE INVENTION

The present invention relates to organosilicon compounds containing dioxolane, diol or diacrylate radicals and to methods for their preparation and use. More specifically, the present invention relates to polymerizable organosilicon compounds, containing one or more silicon-bonded diacrylate radicals, which are prepared from silicon hydride compounds via novel intermediates, and to the use of those polymerizable organosilicon compounds to provide a substrate with a cured coating.

The preparation of organosiloxane compounds containing one or more pendant diol radicals has been suggested by Okazaki et al., U.S. Pat. No. 4,431,789. However, the suggested synthesis method for these compounds comprises the hydrosilylation of an aliphatically unsaturated diol compound with a siloxane hydride. In view of the ready reaction of silicon-bonded hydrogen atoms with alcoholic groups, as well as with aliphatic unsaturation, under such reaction conditions it is likely that a considerable amount of crosslinking occurs, by way of SiOC bond formation and SiC bond formation, and that hydrolyzable gels would be obtained by this method. While the presence of hydrolyzable gels may not be of any substantial consequence for the purposes of patentees, said gels are unacceptable when one desires to use the product as a component in a coating composition.

Organosiloxane-silicate copolymers containing silicon-bonded diol radicals have been disclosed by Pines et al., U.S. Pat. No. 3,337,496. The synthesis route suggested by patentees makes use of silanes which contain epoxy group-containing radicals, said radicals being changed to diol radicals when the silane is hydrolyzed and condensed to form the siloxane-silicate copolymers. The epoxy-containing silanes are said to be available via a hydrosilylation reaction between an aliphatically unsaturated epoxide and a silane hydride. However, the hydrosilylation of epoxides, such as allyl glycidyl ether, is not a straightforward reaction.

On the one hand the hydrosilylation of epoxides with chlorosilanes to provide epoxide-substituted silanes is impossible because of the reaction of the silicon-chlorine linkage with the epoxide ring, as shown by Lavigne et al.; *J. Organometal. Chem.*, 15, 57(1968).

On the other hand the basic nature of the epoxide group tends to poison the usual metal catalysts that are used to promote said reaction and tends to cause a disproportionation reaction to occur with the various hydrolyzable groups that are bonded to the silicon atom of the silane. While it may not be important for patentees' intended use it is unlikely that this synthesis route would lead to diol silanes and siloxanes suitable for the preparation of coating compositions.

Kotzsch et al., U.S. Pat. No. 3,825,567, has addressed the above-noted problems associated with the hydrosilylation of epoxides by hydrosilylating an aliphatically unsaturated dioxolane containing 2,2-dihydro or 2-oxo substitution with a silane hydride and converting the resulting dioxolane-containing silane to an epoxy-containing silane. However, patentees do not suggest any other 2,2-disubstituted dioxolanes or that the dioxolane-containing silanes are useful for preparing diol-containing silanes and siloxanes.

Beckmann et al., U.S. Pat. No. 4,303,739, discloses 4-(methyl-3'-(trimethoxysilyl)-propoxy)-1,3-dioxolane and its use in the preparation of laminated safety glass. Its synthesis is not specifically disclosed and its conversion to an diol-containing silicon compound is not suggested.

Acrylated silicones have been formulated by Watson et al., U.S. Pat. No. 4,331,704, into a radiation-curable varnish for application to uncured, oil-based ink products. While many acrylated silicones, including monoacrylate-monool containing silicones, are referred to by patentees as being suitable for their radiation-curable varnishes, diacrylate-containing silicones are not disclosed or suggested.

BRIEF SUMMARY OF THE INVENTION

The primary object of this invention is to provide new, radiation-curable coating compositions. Another object of this invention is to prepare new silicon compounds which can be used to formulate radiation-curable coating compositions. A further object of this invention is to provide a new method for preparing silicon compounds containing one or more silicon-bonded, difunctional radicals selected from dioxolane-, diol- and diacrylate-functional radicals. Yet another object of this invention is to prepare siloxane polymers of improved purity containing one or more silicon-bonded, difunctional radicals selected from dioxolane-, diol- and diacrylate-functional radicals.

These objects, and others which will become apparent upon consideration of the following disclosure and appended claims, are obtained by the present invention which, briefly stated, comprises preparing new 2-substituted dioxolane-containing silicon compounds via a hydrosilylation reaction and subsequently converting those compounds to diol-, and then to diacrylate-containing silicon compounds, particularly siloxanes.

The diacrylate-containing organosilicon compounds can be applied to a substrate and irradiated to provide a cured silicone coating on the substrate.

DETAILED DESCRIPTION OF THE INVENTION

In a first aspect this invention relates to a method comprising mixing components comprising (i) an amount of a dioxolane compound having the formula

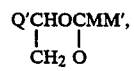

(ii) an amount of a silicon hydride compound containing at least one silicon-bonded hydrogen atom and
(iii) an amount of a hydrosilylation catalyst;
the conditions of said mixing and the amounts of (i), (ii) and (iii) being sufficient to cause a hydrosilylation reaction to occur between the dioxolane compound and the silicon hydride compound, thereby forming a dioxolane-substituted organosilicon compound containing at least one silicon-bonded dioxolane radical having the formula

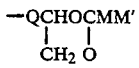

where Q' is a monovalent, aliphatically unsaturated organic radical, M is a monovalent hydrocarbon radical free of aliphatic unsaturation containing from 1 to 6 carbon atoms, M' is H or M, and Q is a divalent organic radical which is bonded to a silicon atom by way of a silicon-carbon bond; all remaining silicon valences of the silicon hydride and of the dioxolane-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms and divalent radicals joining silicon atoms.

In the above formula for the aliphatically unsaturated dioxolane compound (i) Q' denotes a monovalent, aliphatically unsaturated organic radical. While Q' can be any monovalent organic radical containing aliphatic unsaturation which is hydrosilylatable, i.e. reactive with a silicon hydride, hereinafter delineated, it is preferably an olefinically unsaturated radical. Q' is preferably terminally unsaturated, i.e. it has the structure $CH_2=CH-$ where the open valence is bonded directly or indirectly to the #4 atom of the dioxolane moiety.

Optionally, Q' can contain, in addition to carbon and hydrogen, other atoms commonly found in divalent radicals which serve only to link a silicon atom with a specifically selected moiety. Said other atoms include, for example, aprotic oxygen, sulfur and nitrogen atoms. Examples of aprotic O, N and S atoms include oxygen atoms of ethers, esters, amides and ketones; nitrogen atoms of amides and tertiary amines; and the sulfur atoms of thioethers, thioesters and thioketones.

Examples of preferred Q' radicals include $CH_2=CHCH_2OCH_2-$, $CH_2=CH-$, $CH_2=CHCH_2-$, $CH_2=CHCH_2CH_2-$, and $CH_2=CHOCH_2-$.

The M radicals of dioxolane (i) can be any monovalent hydrocarbon radical having from 1 to 6 carbon atoms. They typically have their origin in an aldehyde or ketone that was used to prepare the dioxolane moiety. Therefore they are radicals that allow the facile reaction of the aldehyde or ketone with, for example, a glycol to form the dioxolane moiety. They are also, for the purposes of this invention, radicals that will allow the facile removal of an aldehyde or ketone molecule from the dioxolane ring at an appropriate time in order to provide diol compounds of this invention.

Examples of M radicals include methyl, ethyl, isopropyl, phenyl and cyclohexyl. M' radicals are either hydrogen atoms or M radicals. M and M' can be the same or different, as desired; however, M and M' are preferably both hydrocarbon radicals and most preferably methyl radicals.

Examples of suitable aliphatically unsaturated dioxolanes (i) for the method of this invention include

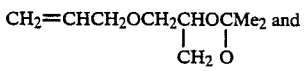

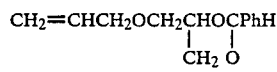

wherein Me denotes the methyl radical and Ph denotes the phenyl radical.

Dioxolanes used in this invention can be prepared from glycols and either an aldehyde such as acetaldehyde or benzaldehyde, thus forming dioxolanes which are cyclic acetals, or a ketone such as acetone or acetophenone, thus forming dioxolanes which are cyclic ketals.

The silicon hydride compound (ii) can have any structure provided that it contains an average of at least one silicon-bonded hydrogen atom per molecule that is available for participation in hydrosilylation. Examples of suitable silicon hydride compounds include silane hydrides and silicon hydrides containing a plurality of silicon atoms such as siloxane hydrides, silcarbane hydrides and siloxane-silcarbane hydrides.

Any silicon valences of the silicon hydride that are not satisfied by hydrogen atoms are satisfied by radicals free of aliphatic unsaturation selected from the group consisting of monovalent hydrocarbon radicals, monovalent halohydrocarbon radicals, monovalent hydrolyzable radicals and divalent radicals joining silicon atoms.

Examples of said divalent radicals joining silicon atoms include oxygen atoms, which provide siloxane bonds; nitrogen atoms, which provide silazane bonds; and aliphatically saturated hydrocarbon, hydrocarbon ether, halohydrocarbon ether and halohydrocarbon radicals, which provide silcarbane bonds. The divalent radicals can be the same or different, as desired; however, they are preferably all oxygen atoms. That is, silicon hydrides (ii) containing a plurality of silicon atoms are preferably siloxane hydrides.

Examples of said monovalent hydrocarbon radicals, herein also referred to as R radicals, include alkyl radicals having from 1 to 20 carbon atoms, such as $CH_3-$, $CH_3CH_2-$, $(CH_3)_2CH-$, $C_6H_{13}-$, $C_8H_{17}-$, $C_{10}H_{21}-$ and $C_{20}H_{41}-$; cycloaliphatic radicals having from 3 to 8 carbon atoms, such as cyclohexyl; aryl radicals having from 6 to 20 carbon atoms, such as phenyl, tolyl, xylyl, anthracyl and xenyl; and aralkyl radicals having from 7 to 20 carbon atoms, such as benzyl and 2-phenylethyl. Typical monovalent hydrocarbon radicals for the purposes of this invention are methyl and phenyl.

Examples of said monovalent halohydrocarbon radicals, herein also referred to as R radicals, include any monovalent hydrocarbon radical delineated above wherein one or more of the hydrogen atoms therein have been replaced with a halogen atom, preferably fluorine or chlorine, but also including bromine and other halogen atoms. Preferred examples thereof include chloroalkyl radicals, such as chloropropyl and chloroisobutyl; fluoroalkyl radicals, such as $C_nF_{2n+1}CH_2CH_2-$ wherein n has a value of from 1 to 10; and halophenyl radicals, such as chlorinated and/or fluorinated phenyl radicals.

Examples of said monovalent hydrolyzable radicals, herein also referred to as Z radicals, include halogen atoms, preferably chlorine; alkoxy radicals, preferably methoxy, ethoxy and isopropoxy; alkoxyalkoxy radicals, such as methoxyethoxy, ethoxyethoxy and methoxyisopropoxy; amido radicals, such as acetamido and N-methylacetamido; and oximo, such as methylethylketoximo.

The silicon hydride (ii) can be any silane hydride having the formula $R_aSiHZ_{(3-a)}$; wherein Z and R denote the above-delineated monovalent hydrolyzable radical and monovalent hydrocarbon and halohydrocarbon radical, respectively, including preferred examples. The value of a can be 0, 1, 2 or 3, thereby encompassing silane hydrides ranging from $R_3SiH$ to $Z_3SiH$. When present, Z is preferably chlorine and R is methyl.

Examples of suitable silane hydrides for the purposes of this invention include $R_3SiH$, such as $Me_3SiH$, $Me_2PhSiH$, $Ph_2MeSiH$, $C_4F_9CH_2CH_2(Me)_2SiH$ and $CF_3CH_2CH_2(Me)_2SiH$; $R_2SiClH$, such as $Me_2SiClH$, $MePhSiClH$, $Ph_2SiClH$, $C_4F_9CH_2CH_2(Me)SiClH$ and $CF_3CH_2CH_2(Me)SiClH$; $RSiCl_2H$, such as $MeSiCl_2H$, $PhSiCl_2H$, $C_4F_9CH_2CH_2SiCl_2H$ and $CF_3CH_2CH_2SiCl_2H$; and $Cl_3SiH$.

The silicon hydride (ii) also can be any siloxane hydride containing at least one siloxane unit having the formula $R_bHSiO_{(3-b)/2}$ and any other siloxane units, if present, having the formula $R_cSiO_{(4-c)/2}$. R denotes the above-delineated monovalent hydrocarbon and halohydrocarbon radical, including preferred examples thereof.

The value of b can be 0, 1 or 2 and the value of c can be 0, 1, 2 or 3, thereby allowing for siloxane units ranging from trisubstituted, i.e. chain-terminating, units to unsubstituted, i.e. network, units.

Examples of typical siloxane units that can be present in the siloxane hydride (ii) include $R_3SiO_{1/2}$ units, such as $Me_3SiO_{1/2}$, $PhMe_2SiO_{1/2}$ and $CF_3CH_2CH_2Me_2SiO_{1/2}$; $R_2HSiO_{1/2}$ units, such as $HMe_2SiO_{1/2}$ and $HPhMeSiO_{1/2}$; $R_2SiO_{2/2}$ units, such as $Me_2SiO_{2/2}$, $MePhSiO_{2/2}$, $CF_3CH_2CH_2MeSiO_{2/2}$, $Ph_2SiO_{2/2}$ and $CF_3CF_2CF_2CH_2CH_2MeSiO_{2/2}$; $RHSiO_{2/2}$, such as $MeHSiO_{2/2}$, $CF_3CH_2CH_2(H)SiO_{2/2}$, $PhHSiO_{2/2}$ and $C_4F_9CH_2CH_2(H)SiO_{2/2}$; $RSiO_{3/2}$ units, such as $MeSiO_{3/2}$, $PhSiO_{3/2}$, $CF_3CH_2CH_2SiO_{3/2}$ and $CF_3CF_2CF_2CH_2CH_2SiO_{3/2}$; $HSiO_{3/2}$; and $SiO_{4/2}$.

While the siloxane hydride (ii) can have any physical form such as a gas, liquid or solid form and any chemical structure such as a linear, cyclic, branch or network structure, it is preferably a liquid material having a linear or cyclic structure described by the formula $(R'Me_2SiO)_w(Me_2SiO)_x(MeR'SiO)_y(MeHSiO)_z$-$(SiMe_2R')_w$ wherein R' denotes a radical selected from the group consisting of said R radicals and hydrogen atoms.

Linear and cyclic siloxane hydrides are preferred as a siloxane hydride reactant (ii) for the preparation dioxolane-containing siloxanes because they provide liquid curable diacrylate-containing compounds compositions which are effective as a curable component in coating compositions, particularly adhesive-release coating compositions.

In this formula the values of x, y, z and x+y+z have average values of zero or more and both w have a value of zero or 1, with the proviso that there is an average of at least one silicon-bonded hydrogen atom per molecule of siloxane hydride.

For example, for linear siloxane hydrides having the above formula each w has a value of 1 and x+y+z has an average value of 0 or more, thereby providing a siloxane hydride having the formula $R'Me_2SiO(Me_2SiO)_x(MeR'SiO)_y(MeHSiO)_z$-$SiMe_2R'$ and a viscosity of as little as 1 centistoke to as much as several million centistokes at 25° C.

Preferred examples of said linear siloxane hydrides include $Me_3SiO(Me_2SiO)_x(MeHSiO)_zSiMe_3$;

$HMe_2SiO(Me_2SiO)_xSiMe_2H$ and $HMe_2SiO(Me_2SiO)_x(MeHSiO)_zSiMe_2H$, wherein z has a value of from 1 to, for example, 50 and x has a value of from, for example, zero to several hundred.

Additional examples of said linear siloxane hydrides include $Me_3SiO(Me_2SiO)_x(MeRSiO)_y(MeHSiO)_zSiMe_3$;

$HMe_2SiO(Me_2SiO)_x(MeRSiO)_ySiMe_2H$, and $HMe_2SiO(Me_2SiO)_x(MeRSiO)_y(MeHSiO)_zSiMe_2H$, wherein R denotes, for example, a phenyl radical, an alkyl radical or a fluorinated radical such as $CF_3CH_2CH_2-$ or $CF_3CF_2CF_2CH_2CH_2-$, x has a value of from, for example, zero to several hundred, y has a value of from 1 to, for example, several hundred and z has a value of from 1 to, for example, 50.

For cyclic siloxane hydrides having the above formula each w has a value of 0 and x+y+z has an average value of 3 or more, thereby providing liquid or low-melting siloxane hydrides having the formula $(Me_2SiO)_x(MeR'SiO)_y(MeHSiO)_z$ and a viscosity of as little as 1 centistoke at 25°.

Examples of said cyclic siloxane hydrides include $(Me_2SiO)_x(MeHSiO)_z$ and $(Me_2SiO)_x(MeRSiO)_y(MeHSiO)_z$;

wherein R denotes, for example, a phenyl radical, an alkyl radical or a fluorinated radical such as $CF_3CH_2CH_2-$ or $CF_3CF_2CF_2CH_2CH_2-$, x has a value of from, for example, zero to 10, y has a value of from 1 to, for example, 10 and z has a value of from 1 to, for example, 10. Poly(methylhydrogen) cyclosiloxanes having up to 10 silicon atoms are preferred cyclic siloxane hydrides.

The silicon hydride (ii) also can be any silcarbane hydride or siloxane-silcarbane hydride. Silcarbane hydrides are known compounds similar in structure to siloxane hydrides wherein the oxygen atom bonding silicon atoms has been replaced with a divalent organic radical, thereby providing silicon-carbon bonding rather than silicon-oxygen bonding in the polymer backbone. Typical examples of said divalent organic radicals have been noted above. Typical examples of silcarbane hydrides include silethylene hydrides and silphenylene hydrides.

In addition to the above-delineated compounds, silicon hydride (ii) can also comprise silicon compounds containing silicon atoms bearing more than one hydrogen atom; however, such silicon multihydrides are more difficult to handle than the silicon hydrides delineated above.

The hydrosilylation catalyst (iii) can be any of the well known agents that are effective for facilitating the addition of the elements of the silicon-hydrogen linkage to a site of aliphatic unsaturation, particularly terminal olefinic unsaturation. Hydrosilylation catalysts include free radical initiators, photoinitiators and precious metal compounds.

Examples of suitable free radical initiators include, but are not limited to, redox pairs, perborates, percarbonates, photochemical systems, azo compounds such as azo-bis(isobutyronitrile), acyl peroxides such as benzoyl peroxide, alkyl peroxides such as di-t-butyl peroxide and hydroperoxides such as cumene hydroperoxide.

Examples of suitable photoinitiators include, but are not limited to, benzoin, benzoin alkyl ethers such as methyl, ethyl, isopropyl or isobutyl benzoin ether, acetophenone derivatives such as dialkoxyacetophenone such as diethoxyacetophenone, di-and trichloroacetophenones, α,α-dimethoxy-α-phenylacetophenone, 1-hydroxycyclohexylphenyl ketone, 2-hydroxy-2-methyl-1-phenylpropane-1-one, methylphenyl glyoxylate, 4-benzoylbenzyltrimethylammonium chloride, α-acyloxime esters such as 1-phenyl-1,2-propanedione-2-(O-ethoxycarbonyloxime), thioxanthane and its derivatives, benzophenone in combination with a chain transfer agent such as a NH group and azo-bis(isobutyronitrile).

Examples of precious metal-containing compounds include, but are not limited to, platinum group metal-containing catalyst compounds. By platinum group it is meant herein ruthenium, rhodium, palladium, osmium, iridium and platinum. Component (iii) can be a platinum group metal; a carrier, such as silica gel or powdered charcoal, bearing a platinum group metal; or a compound or complex of a platinum group metal.

A preferred platinum-containing catalyst component in the method of this invention is a form of chloroplatinic acid, either as the commonly available hexahydrate form or as the anhydrous form, because of its easy dispersibility in organosilicon systems. A particularly useful form of chloro-platinic acid is that composition obtained when it is reacted with an aliphatically unsaturated organosilicon compound such as divinyltetramethyldisiloxane, as disclosed by Willing, U.S. Pat. No. 3,419,593 incorporated herein by reference.

The amount of hydrosilylation catalyst (iii) that is used in the method of this invention is not narrowly limited as long as there is a sufficient amount to accelerate a reaction between the silicon-bonded hydrogen atoms of silicon hydride (ii) with the aliphatic unsaturation of the dioxolane compound (i). The exact necessary amount of said catalyst component will depend upon the particular catalyst and is not easily predictable. However, for chloroplatinic acid said amount can be as low as one part by weight of platinum for every one million parts by weight of (i) plus (ii). Preferably said amount is at least 10 parts by weight, on the same basis.

The relative amounts of dioxolane compound (i) and silicon hydride compound (ii) that are used in the method of this invention are not critical, the only requirement pertinent thereto being that there must be a sufficient amount of the former so that the product of the reaction contains an average of at least one silicon-bonded dioxolane radical having the above-stated formula.

The method of this invention can be practiced so that the product contains any number of unreacted silicon-bonded hydrogen atoms, in addition to said dioxolane radicals, if desired. Alternatively, the method can be practiced in such a manner that substantially all of the silicon-bonded hydrogen atoms have been reacted, if desired.

The required amounts of components (i) and (ii) can be calculated from a knowledge of the silicon-bonded hydrogen content of the silicon hydride, the desired number of silicon-bonded hydrogen atoms to be reacted and the stoichiometry of the following generalized hydrosilylation reaction:

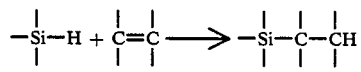

Although this reaction requires one site of aliphatic unsaturation for every silicon-bonded hydrogen atom to be reacted it is typical, especially when all silicon-bonded hydrogen atoms are to be reacted, that a slight excess of the former be used to insure that the reaction takes place to the desired extent.

The method of this invention can be practiced in any suitable manner that will cause said hydrosilylation to occur. For example, when the hydrosilylation catalyst (iii) comprises a platinum-containing material the reaction will generally occur at room temperature and nothing more than mere mixing of the required reactants is required. However, it is generally desired to accelerate the reaction further and heating can be advantageously used to this end.

One or more solvents can be mixed with reactants (i), (ii) and (iii), if desired, to facilitate the reaction and/or the handling of the reactants and/or the products. Said solvents must not interfere with the desired hydrosilylation reaction and preferably should not react with the reactants or products of this method.

Suitable solvents include the aliphatically saturated hydrocarbons, esters, ketones, halocarbons, ethers and alcohols that are commonly used in the organosilicon art. Examples thereof include hexane, toluene, xylene, ethyl acetate, methyl isobutyl ketone, trichloroethylene, diethyl ether, dioxane, ethylene glycol dimethyl ether, methanol, ethanol and isopropanol.

Said solvents can be used in the other aspects of this invention, delineated below with the same limitations relating to unreactivity.

In summary, the first aspect of the method of this invention, as above-delineated, comprises the formation of a dioxolane-substituted organosilicon compound containing at least one silicon-bonded dioxolane radical having the formula

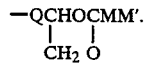

This first aspect of this invention further relates to the dioxolane-substituted organosilicon compounds, hereinafter delineated, that are prepared by this method.

Dioxolane-substituted organosilanes of this invention have the formula

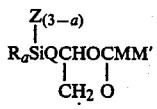

where Z is said monovalent hydrolyzable radical, a has a value of 0, 1, 2 or 3 and R is said monovalent hydrocarbon and halohydrocarbon radical. Preferred embodiments thereof include those organosilicon compound wherein Z is chlorine, R is Me and each of said dioxane radicals has the formula

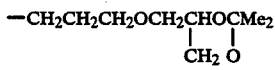

where Me is a methyl radical.

Dioxolane-substituted organosiloxanes of this invention contain at least one organosiloxane unit having the formula

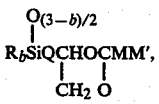

examples of which include the above-delineated siloxane hydride units where the silicon-bonded hydrogen has been replaced with a dioxolane radical. All other siloxane units therein, if any, have the formula $R_cH_dSiO_{(4-c-d)/2}$, such as those delineated above.

In the above unit formulae b has a value of 0, 1 or 2, c and c+d have values of 0, 1, 2 or 3, d has a value of 0 or 1 and R is said monovalent hydrocarbon and halohydrocarbon radical.

Preferred dioxolane-substituted organosiloxanes of this invention have the formula $(XMe_2SiO)_w(Me_2SiO)_x(MeXSiO)_y(MeHSiO)_z$-$(SiMe_2X)_w$ where X is selected from the group consisting of R radicals, hydrogen atoms, and dioxolane radicals.

The average values of x, y and z can be zero or more, with the following provisos. For linear organosiloxanes each w has a value of 1 and x+y+z has an average value of 0 or more and for cyclic organosiloxanes each w has a value of 0 and x+y+z has an average value of at least 3, there being an average of at least one of said silicon-bonded dioxolane radicals per molecule of organosiloxane. Each of said dioxolane radicals preferably has the formula

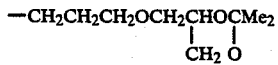

where Me is a methyl radical.

Examples of said preferred dioxolane-substituted organosilanes and organosiloxanes include those silane and siloxane hydrides delineated above wherein at least one of the silicon-bonded hydrogen atoms in each molecule has been replaced with a dioxolane radical, preferably

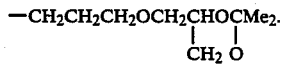

The dioxolane-substituted organosilicon compounds are useful in a second aspect of this invention which comprises mixing with the dioxolane-substituted organosilicon compound containing at least one silicon-bonded dioxolane radical (iv) an amount of an olysis agent comprising a compound selected from the group consisting of hydrolysis compounds and alcoholysis compounds, the conditions of said mixing and the amount of olysis agent being sufficient to convert said dioxolane radicals to diol radicals, thereby forming an diol-substituted organosilicon compound containing at least one silicon-bonded diol radical having the formula

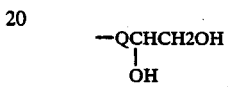

where Q has the stated meaning; all remaining silicon valences of the diol-substituted organosilicon compound being satisfied by radicals free of aliphatic unsaturation selected from the group consisting of monovalent hydrocarbon radicals, monovalent halohydrocarbon radicals, monovalent hydrolyzable radicals, hydroxyl radicals, hydrogen atoms and divalent radicals joining silicon atoms.

In this second aspect of the invention an olysis agent is used to convert the dioxolane radicals to diol radicals. Of course, any silicon-bonded hydrolyzable groups present in the organosilicon compound may be affected by this olysis agent and silicon compounds containing silicon-bonded hydroxyl radicals, in addition to said silicon-bonded diol radicals and monovalent hydrocarbon radicals, monovalent halohydrocarbon radicals, monovalent hydrolyzable radicals, hydrogen atoms and divalent radicals joining silicon atoms, hereinabove delineated, may be obtained.

The dioxolane-substituted organosilicon compounds that are used in this aspect of the invention are those delineated above, including preferred embodiments thereof, and those in the examples disclosed below.

The olysis agent (iv) can be any means which comprises an hydrolysis and/or alcoholysis compound. Examples of hydrolysis compounds include water in gas, liquid or solid form, and water-providing compounds. Examples of alcoholysis compounds include alcohols, such as methanol and ethanol; glycols, such as ethylene glycol; and polyols. The olysis agent can further comprise a carrier for the hydrolysis and/or alcoholysis compound, such as a solvent.

The relative amounts of dioxolane-substituted organosilicon compound and olysis agent (iv) that are used in the method of this invention are not critical, the only requirement pertinent thereto being that there must be a sufficient amount of the latter so that the product of the reaction contains an average of at least one silicon-bonded diol radical having the above-stated formula. Preferably, the method is practiced in such a manner that substantially all of the silicon-bonded dioxolane radicals are converted to said diol radicals and all silicon-bonded hydrolyzable radicals, if any, are removed.

The required minimum amount of component (iv) can be calculated from a knowledge of the hydrolyzable group content of the dioxolane-substituted organosilicon compound and the stoichiometry of the following generalized reactions:

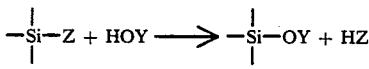

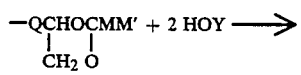

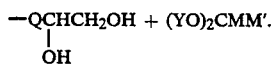

Although these reactions require one molecule of olysis agent, HOY (Y denotes H or an organic radical such as methyl or hydroxyethyl), for every silicon-bonded Z and two for every dioxolane radical it is typical that a large excess of the olysis agent be used to insure that the reaction takes place to the desired extent.

The method of this invention can be practiced in any suitable manner. For example, when the olysis agent is water the reaction will generally occur at room temperature and nothing more than mere mixing of the required reactants is required. However, it is generally desired to accelerate the reaction further and heating can be advantageously used to this end. When the olysis agent is an alcohol it is preferred to catalyze the alcoholysis reaction with, for example HCl or $CF_3SO_3H$.

In summary, the second aspect of the method of this invention, as above-delineated, comprises the formation of a diol-substituted organosilicon compound, hereinafter further delineated, containing at least one silicon-bonded diol radical having the formula

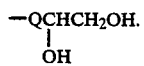

This second aspect of the invention further relates to the diol-substituted organosilicon compounds that are prepared by this method.

Diol-substituted organosilanes of this invention have the formula

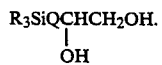

Embodiments thereof where Q is $-CH_2CH_2CH_2OCH_2-$ are preferred.

Diol-substituted organosiloxanes of this invention contain at least one organosiloxane unit having the formula

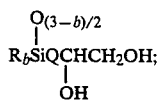

examples of which include the above-delineated siloxane hydride units where the silicon-bonded hydrogen has been replaced with a diol radical. All other siloxane units therein, if any, have the formula $R_cH_dSiO_{(4-c-d)/2}$, such as those delineated above.

In the above unit formulae b has a value of 0, 1 or 2, c and c+d have values of 0, 1, 2 or 3, d has a value of 0 or 1 and R is said monovalent hydrocarbon and halohydrocarbon radical.

Preferred diol-substituted organosiloxanes of this invention have the formula

where Me is methyl, L is selected from the group consisting of R radicals, hydrogen atoms, and diol radicals. As noted above for siloxane hydrides, x, y and z have average values of 0 or more with the provisos that for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded diol radicals per molecule of organosiloxane. Each of said diol radicals preferably has the formula

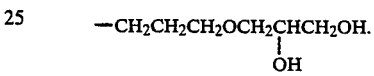

Examples of said preferred diol-substituted organosiloxanes include those siloxane hydrides delineated above wherein at least one of the silicon-bonded hydrogen atoms in each molecule has been replaced with a diol radical, preferably

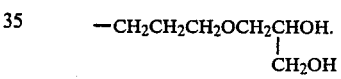

The diol-substituted organosilicon compounds are useful in a third aspect of this invention which comprises mixing with the diol-substituted organosilicon compound containing at least one silicon-bonded diol radical.

(v) an amount of an acryl compound having the formula

where R" is H or $CH_3$ and G is selected from the group consisting of halogen, hydroxy, alkoxy and $CH_2=CR''CO_2-$, said amount of acryl compound and the conditions of said mixing being sufficient to convert said diol radicals to diacrylate radicals, thereby forming a diacrylate-substituted organosilicon compound containing at least one silicon-bonded diacrylate radical having the formula

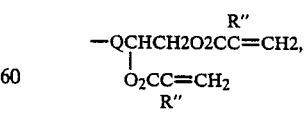

where Q and R" have the stated meanings, all remaining silicon valences of the diacrylate-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms and divalent radicals joining silicon atoms.

In this third aspect of the invention an acryl compound is used to convert the diol radicals to diacrylate radicals. Of course, any silicon-bonded hydroxyl groups present in the diol-substituted organosilicon compound can be affected by this acryl compound and silicon compounds containing silicon-oxygen bonded acryloxy radicals, in addition to said silicon-bonded diacrylate radicals and monovalent hydrocarbon radicals, monovalent halohydrocarbon radicals, monovalent hydrolyzable radicals, hydrogen atoms and divalent radicals joining silicon atoms, hereinabove delineated, may be obtained.

The diol-substituted organosilicon compounds that are used in this aspect of the invention are those delineated above, including preferred embodiments thereof, and those disclosed in the examples below.

The acryl compound (v) can be any compound having the formula CH$_2$=CR"COG which will convert a carbinol group to an acrylate or methacrylate group. Examples of suitable acryl compounds include acrylic and methacrylic acids, acrylyl and methacrylyl chloride, acrylic and methacrylic anhydride and acrylic and methacrylic esters, such as methyl methacrylate and ethyl acrylate.

The acryl compound can further comprise an acidic or alkaline catalyst to accelerate the conversion of the diol radicals to diacrylate radicals.

The relative amounts of diol-substituted organosilicon compound and acryl compound (v) that are used in the method of this invention are not critical, the only requirement pertinent thereto being that there must be a sufficient amount of the latter so that the product of the reaction contains an average of at least one silicon-bonded diacrylate radical having the above-stated formula. Preferably, the method is practiced in such a manner that substantially all of the silicon-bonded diol radicals are converted to said diacrylate radicals.

The required minimum amount of component (v) can be calculated from a knowledge of the diol-radical content of the diol-substituted organosilicon compound and the stoichiometry of the following generalized reactions:

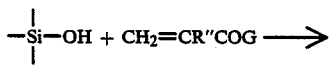

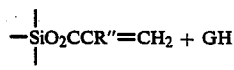

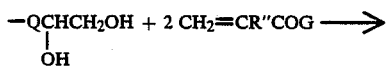

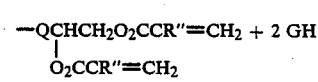

Although these reactions require one molecule of acryl compound for every silicon-bonded OH and two molecules of acryl compound for every diol radical it is typical that a large excess of acryl compound be used to insure that the reaction takes place to the desired extent.

The method of this invention can be practiced in any suitable manner. For example, when the G radical of the acryl compound is chlorine or acryloxy the reaction will generally occur at room temperature and nothing more than mere mixing of the required reactants is required. However, it is generally desired to accelerate the reaction further and heating can be advantageously used to this end. When the G radical of the acryl compound is hydroxy or alkoxy the reaction typically needs heating and catalyzing with an acidic or an alkaline material.

In summary, the third aspect of the method of this invention, as above-delineated, comprises the formation of an diacrylate-substituted organosilicon compound, hereinafter further delineated, containing at least one silicon-bonded diacrylate radical having the formula

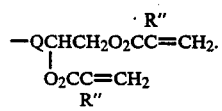

The third aspect of this invention further relates to the diacrylate-substituted organosilicon compounds that are prepared by this method, and curable coating compositions comprising said compounds.

Diacrylate-substituted organosilanes of this invention have the formula

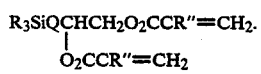

Embodiments thereof where Q is —CH$_2$CH$_2$CH$_2$OCH$_2$— are preferred.

Diacrylate-substituted organosiloxanes of this invention contain at least one organosiloxane unit having the formula

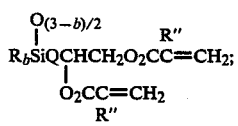

examples of which include the above-delineated siloxane hydride units where the silicon-bonded hydrogen has been replaced with a diacrylate radical. All other siloxane units therein, if any, have the formula R$_c$H$_d$SiO$_{(4-c-d)/2}$, such as those delineated above.

In the above unit formulae b has a value of 0, 1 or 2, c and c+d have values of 0, 1, 2 or 3, d has a value of 0 or 1 and R is said monovalent hydrocarbon and halohydrocarbon radical.

Preferred diacrylate-substituted organosiloxanes of this invention have the formula

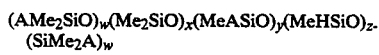

where Me is the methyl radical, A is selected from the group consisting of R radicals, hydrogen atoms, and diacrylate radicals.

As noted above for siloxane hydrides, x, y and z have average values of 0 or more with the provisos that for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded diacrylate radicals per molecule of organosiloxane. Preferably, each of said diacrylate radicals has the formula

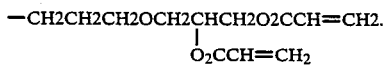
—CH2CH2CH2OCH2CHCH2O2CCH=CH2.
|
O2CCH=CH2

Examples of said preferred diacrylate-substituted organosiloxanes include those siloxane hydrides delineated above wherein at least one of the silicon-bonded hydrogen atoms in each molecule has been replaced with a diacrylate radical, preferably

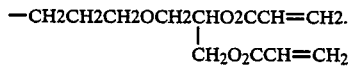
—CH2CH2CH2OCH2CHO2CCH=CH2.
|
CH2O2CCH=CH2

The diacrylate-substituted organosilicon compounds of this invention, delineated above, including preferred embodiments thereof, can further comprise components that are typically used in radiation-curable coating compositions containing acrylate-containing compounds. Examples of said other components include diluents, including solvents and reactive diluents; curing aids, such as photoinitiators, photosensitizers and catalysts; and, for adhesive-releasing coating compositions, controlled release additives, such as siloxane resins and organofunctional siloxanes.

The diacrylate-substituted organosilicon compounds are useful in a fourth aspect of this invention which comprises a process comprising applying a composition comprising a diacrylate-substituted organosilicon compound to a substrate and thereafter exposing the applied coating to acrylate-polymerizing radiation until said organosilicon compound has been converted to the solid state, said organosilicon compound contains at least one silicon-bonded diacrylate radical having the formula

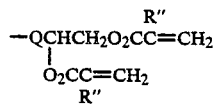
R"
—QCHCH2O2CC=CH2
|
O2CC=CH2
R"

where Q is a divalent organic radical which is bonded to the silicon atom by way of a silicon-carbon bond and R" is H or CH3; all remaining silicon valences of the diacrylate-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms and divalent radicals joining silicon atoms.

In the process of this invention the organosilicon compound to be applied to a substrate can be any of the diacrylate-substituted organosilicon compounds delineated above, including preferred embodiments thereof.

Examples of substrates that can be coated by the process of this invention include flexible substrates such as paper, metal foil, polymer films, optical fibers and textiles and relatively non-flexible substrates such as polymer laminates, such as circuit boards, siliceous substrates such as ceramic, glass and brick, wood substrates and molded, cast and stamped metal articles, the curable coatings of this invention are useful in the adhesive release art, the electronic art such as encapsulating and photoresist, the graphic art etc.

The coating composition of this invention can be applied to substrates of various compositions, shapes, sizes and uses. In a preferred embodiment of this process a flexible substrate is coated for the purpose of providing for the substrate an adhesive-releasing surface.

When the diacrylate-substituted siloxanes of this invention are applied to a substrate and polymerized siloxane-substituted polyacrylate coatings are provided. Depending on the relative siloxane content of the coating composition the cured coating are expected to have physical properties ranging from those like the polyacrylates to those like the polyorganosiloxanes.

In the process of this invention a thin coating, for example up to 1 mm in thickness, of the coating composition is applied in the well known manner, for example spraying, rolling, spreading or brushing, and thereafter, such as immediately or shortly thereafter, exposed to the radiation.

In the adhesive-releasing art a flexible substrate such as paper, polymer film, polymer-coated paper or metal foil is rendered adhesive-releasing by the application of a curable fluid composition to the flexible substrate at a coating weight of from 0.5 to 2 pounds per ream of substrate. After the applied composition has been cured the thus-treated surface is brought into adhesive contact with an adhesive, either free or disposed on a surface of an article. The adhesive-releasing surface thereby serves as a protective layer for one surface of the adhesive until the adhesive is to be used, whereupon it can be readily removed from the adhesive.

The applied coating can be cured by any suitable means such as chemical, radiant or thermal means. When the applied coating is to be cured by thermal or ultra-violet radiation, the applied composition should contain a polymerization initiator. In a preferred embodiment of this invention the applied composition is cured with electron beam radiation and the composition needs no added initiator.

The radiation that is used to cure the applied coating composition can be any radiation that is effective for initiating a polymerization of acrylic esters, such as the well known electron beam and/or ultraviolet radiations. For more detailed information the reader is referred to any of the standard references that teach the polymerization of acryl-containing monomers. Included herein by reference are *Kirk-Othmer Encyclopedia of Chemistry and Technology*; John Wiley and Sons, N.J., Second Edition, 1972, Vol. I, pp. 274 to 284 and *Encyclopedia of Polymer Science and Technology*; John Wiley and Sons, N.J., 1966, Vol. I, pp. 177 to 197.

The following examples are disclosed to further illustrate, but not limit, the invention delineated by the appended claims. All parts and percentages are by weight and all temperatures are Celsius degrees unless otherwise stated. Me, Ph and Vi denote the methyl, phenyl and vinyl radicals, respectively.

All dioxolane-substituted organosilicon compounds were characterized by proton nuclear magnetic resonance spectroscopy (nmr) and by infrared spectroscopy (ir). They all showed two singlets at δ=1.3 (from tetramethylsilane) in the nmr and doublets at 1375 cm−1 in the ir characteristic of the isopropylidene group of the methylenedioxolane moiety.

All diol-substituted organosilicon compounds were characterized by nmr and by ir. They all showed the absence of the two singlets at δ=1.3 in the nmr and doublets at 1375 cm−1 in the ir that were characteristic of the isopropylidene group of the methylenedioxolane moiety and the presence of a prominent absorption at 3600 cm−1 in the ir characteristic of carbinol OH.

The following two examples illustrate the preparation of dioxolane-substituted silanes of this invention using the method of this invention.

EXAMPLE 1

Five parts of 4-allyloxymethyl-2,2-dimethyl-1,3-dioxolane and 0.002 part of (PhC≡CC(OH)(CH₃)Ph)₂Pt, a hydrosilylation catalyst, were mixed in a flask fitted with a condenser, an addition funnel and a thermometer. Methyldichlorosilane, 3.5 parts, was added to the mixture via the addition funnel and the mixture was heated to 71°. At 78° a mild exotherm occurred which raised the reaction temperature to 91°. After the exotherm had subsided the reaction mixture was distilled at reduced pressure to give 6.5 parts of 4-(3'-methyldichlorosilylpropoxymethyl)-2,2-dimethyl-1,3-dioxolane having a boiling point of 100° to 103° at 0.7 Torr.

The 4-allyloxymethyl-2,2-dimethyl-1,3-dioxolane was prepared by mixing acetone, 225 parts, 3-allyloxy-1,2-propanediol, 195 parts and toluene, 480 parts in a flask fitted with a magnetic stirring bar and a water trap mounted with a reflux condenser. Concentrated sulfuric acid, 4 parts, was added to the flask and the mixture was heated to reflux. The first 170 parts of distillate were removed via the water trap, after which reflux was conducted and water was collected in the water trap. After 13 hours the reaction mixture was cooled, neutralized with aqueous sodium bicarbonate, distilled to remove water and toluene and then distilled under vacuum to give 161 parts of 4-allyloxymethyl-2,2-dimethyl-1,3-dioxolane having a boiling point of 57° to 58° at 4.5 Torr.

EXAMPLE 2

Five parts of 4-allyloxymethyl-2,2-dimethyl-1,3-dioxolane and 0.002 part of (PhC≡CC(OH)(CH₃)Ph)₂Pt were mixed in a flask fitted with a condenser, an addition funnel and a thermometer. Dimethylchlorosilane, 5 parts, was added to the mixture via the addition funnel and the mixture was heated to 70° for 25 minutes. The reaction mixture was then cooled and distilled at reduced pressure to give 5.2 parts of 4-(3'-dimethylchlorosilylpropoxymethyl)-2,2-dimethyl-1,3-dioxolane having a boiling point of 98° to 105° at 0.7 Torr.

The following two examples illustrate the preparation of dioxolane-substituted organosiloxanes of this invention using the method of this invention.

EXAMPLE 3

Twenty parts of 4-allyloxymethyl-2,2-dimethyl-1,3-dioxolane, 0.006 part of a hydrosilylation catalyst containing 4% platinum and being prepared according to the method of Willing, U.S. Pat. No. 3,419,593, and 80 parts of a hydrogen-terminated polydimethylsiloxane containing an average of about 20 silicon atoms per molecule were mixed in a flask. A mild exotherm took place which raised the temperature of the reaction mixture to 70° and external heating was used to keep it there for 5 hours. An infrared spectrum of the reaction mixture taken after five hours showed that no silicon-bonded hydrogen atoms remained. The product was assigned the structure XMe₂SiO(Me₂SiO)₁₈SiMe₂X wherein X denotes

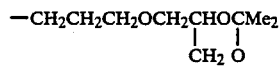

based on the spectroscopic data and the nature of the hydrosilylation reaction.

EXAMPLE 4

Twenty-five and 9/10 parts of 4-allyloxymethyl-2,2-dimethyl-1,3-dioxolane, 0.02 part of the hydrosilylation catalyst described in Example 3 and 41.4 parts of a hydrogendimethylsiloxane-terminated polydimethylsiloxane-co-methylhydrogensiloxane containing an average of about 14 dimethylsiloxane units and 2 methylhydrogensiloxane units per molecule were mixed in a flask. A mild exotherm took place and external heating was used to keep the temperature of the reaction mixture at 70° for 24 hours. An infrared spectrum of the reaction mixture taken after 24 hours showed that no silicon-bonded hydrogen atoms remained. The product was assigned the structure $$XMe_2SiO(Me_2SiO)_{14}(MeXSiO)_2SiMe_2X$$

wherein X denotes

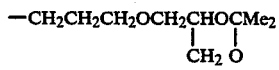

based on the spectroscopic data and the nature of the hydrosilylation reaction.

The following three examples illustrate the preparation of diol-substituted organosiloxanes of this invention using the method of this invention.

EXAMPLE 5

The silane of this invention that is disclosed in Example 1, 4.4 parts, was added to 15 parts of distilled water. After 5 minutes a homogeneous solution was obtained which was freed of water by distillation to leave a highly viscous residue. The residue was assigned the structure

wherein y had a value of three or more.

EXAMPLE 6

The silane of this invention that is disclosed in Example 2, 2 parts, was added to 2 parts of distilled water. A homogeneous solution was obtained which was heated to 90° for 10 minutes and then distilled under reduced pressure to yield 1.02 parts of a viscous distillate having a boiling point of 232° to 234° at 0.7 Torr. The residue was assigned the structure

based on its nmr and ir spectra.

EXAMPLE 7

The siloxane of this invention that is disclosed in Example 3, 98 parts, was added to 30 parts of methanol containing 3 parts of concentrated hydrochloric acid. The reaction mixture was distilled to a head temperature of 74° to remove methanol and leave a highly viscous residue which was further devolatilized at 80° and 30 Torr. The residue was cooled and filtered to give 83.5 parts of a viscous fluid having a carbinol content of 4.0%; theoretical carbinol content 4.0%. The fluid was assigned the structure $LMe_2SiO(Me_2SiO)_{18}SiMe_2L$ wherein L denotes the diol radical —$CH_2CH_2CH_2OCH_2CH(OH)CH_2OH$.

The following three examples illustrate the preparation of silanes and siloxanes of this invention using other silanes and siloxanes of this invention.

EXAMPLE 8

The silane of this invention that is disclosed in Example 2 was converted to another silane of this invention by mixing 50.3 parts thereof with 32 parts of sodium N-methylacetamide in toluene. After the exothermic reaction subsided the mixture was stirred for two hours. The reaction product was filtered, the filtrate was concentrated by evaporation and the concentrate was distilled under reduced pressure to give 41.3 parts of the desired 4-(3'-N-methylacetamidodimethylsilylpropoxymethyl)-2,2-dimethyl-1,3-dioxolane having a boiling point of 140° to 143° at 2 Torr. The nmr of the distillate showed that the dioxolane moiety was intact.

EXAMPLE 9

A siloxane of this invention having the formula $LMe_2SiO(Me_2SiO)_{14}SiMe_2L$ wherein L denotes the diol radical —$CH_2CH_2CH_2OCH_2CH(OH)CH_2OH$, 14.33 parts, was mixed with 100 parts of octamethylcyclotetrasiloxane and 0.2 part of trifluoromethanesulfonic acid and the mixture was stirred and heated at 70° for 3 hours. The highly viscous fluid was neutralized with calcium carbonate and filtered to give a colorless fluid having a carbinol content of 0.69% (theoretical 0.59%) and the formula $LMe_2SiO(Me_2SiO)_{151}SiMe_2L$ wherein L denotes the diol radical —$CH_2CH_2CH_2OCH_2CH(OH)CH_2OH$.

EXAMPLE 10

A siloxane of this invention having the formula $LMe_2SiO(Me_2SiO)_{14}SiMe_2L$ wherein L denotes the diol radical —$CH_2CH_2CH_2OCH_2CH(OH)CH_2OH$, 31.6 parts, was mixed with 0.5 part of KOH, 6.96 parts of aminoethylaminoisobutyl-methyldimethoxysilane and 100 parts of octamethylcyclotetrasiloxane and the mixture was stirred and heated at 150° for 6 hours. The highly viscous fluid was neutralized with carbon dioxide and 5 parts of Fuller's Earth was added. The product was filtered to give a yellow colored fluid having a carbinol+amino content of 1.63% (theoretical 1.70%) and the formula $LMe_2SiO(Me_2SiO)_{96}(MeRSiO)_2SiMe_2L$ wherein L denotes the radical —$CH_2CH_2CH_2OCH_2CH(OH)CH_2OH$ and R denotes the radical —$CH_2CH(CH_3)CH_2NHCH_2CH_2NH_2$.

The following three examples illustrate the preparation and use of diacrylyloxy-substituted organosiloxanes of this invention using the methods of this invention.

EXAMPLE 11

The siloxane of this invention disclosed in Example 7 and having the structure $LMe_2SiO(Me_2SiO)_{18}SiMe_2L$, 12.6 parts, was mixed with 0.06 part of hydroquinone, 0.03 part of concentrated sulfuric acid, 18 parts of toluene and 2.5 parts of acrylic acid in a flask fitted with a water trap topped with a condenser. The reaction mixture was heated to reflux and all of the water of reaction was collected in the trap. The reaction product was then devolitilized at 50° and 30 Torr to provide the desired siloxane having the formula $AMe_2SiO(Me_2SiO)_{18}SiMe_2A$ wherein A denotes the diacrylyloxy radical having the formula

—$CH_2CH_2CH_2OCH_2CH(O_2CCH=CH_2)CH_2O_2CCH=CH_2$.

EXAMPLE 12

Two parts of the siloxane disclosed in Example 11 and having the formula $AMe_2SiO(Me_2SiO)_{18}SiMe_2A$ was mixed with 0.1 part of Irgacure 500 photoinitiator and the resulting mixture was coated onto supercalendered kraft paper. The coated paper was passed under two ultraviolet lamps at a speed of 45 feet per minute which cured the coating to an adhesive releasing coating having no smear, no rub-off and no migration.

EXAMPLE 13

The siloxane disclosed in Example 11 and having the formula $AMe_2SiO(Me_2SiO)_{18}SiMe_2A$ was coated onto supercalendered kraft paper and the coated paper was exposed to 5 megarad of electron beam radiation which cured the coating to an adhesive releasing coating having no smear, no rub-off and no migration.

That which is claimed is:

1. A method comprising mixing components comprising
   (i) an amount of a dioxolane compound having the formula

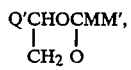

(ii) an amount of a silicon hydride compound containing at least one silicon-bonded hydrogen atom, the relative amounts of (i) and (ii) being sufficient to provide one site of aliphatic unsaturation for every silicon-bonded hydrogen atom to be reacted and
   (iii) an amount of a hydrosilylation catalyst sufficient to accelerate a reaction between the silicon-bonded hydrogen atoms of the silicon hydride with the aliphatic unsaturation of the dioxolane compound; and causing, by heating the mixture, or allowing a hydrosilylation reaction to occur between the dioxolane compound and the silicon hydride compound, thereby forming a dioxolane-substituted organosilicon compound containing at least one silicon-bonded dioxolane radical having the formula

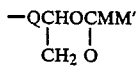

where Q' is a monovalent, aliphatically unsaturated organic radical, M is a monovalent hydrocarbon radical free of aliphatic unsaturation containing from 1 to 6 carbon atoms, M' is H or M, and Q is a divalent organic radical which is bonded to a silicon atom by way of a silicon-carbon bond; all remaining silicon valences of the silicon hydride and of the dioxolane-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms, divalent radicals joining silicon atoms and mixtures thereof.

2. A method according to claim 1 wherein the silicon hydride compound is a silane hydride having the formula $R_aSiHZ_{(3-a)}$; where Z is said monovalent hydrolyzable radical, a has a value of 0, 1, 2 or 3 and R is said monovalent hydrocarbon or halohydrocarbon radical.

3. A method according to claim 2 wherein Z is chlorine, R is Me and the dioxolane compound has the formula

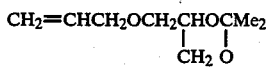

where Me is a methyl radical.

4. A method according to claim 1 wherein the silicon hydride is a siloxane hydride having the formula

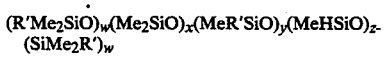

where Me is the methyl radical, R' is selected from the group consisting of hydrogen atoms and said monovalent hydrocarbon and halohydrocarbon radicals, x, y and z have average values of 0 or more and, for linear siloxane hydrides each w has a value of 1 and x+y+z has an average value of 0 or more and for cyclic siloxane hydrides each w has a value of 0, x+y+z has an average value of at least 3, there being an average of at least one silicon-bonded hydrogen atom per molecule of siloxane hydride.

5. A method according to claim 4 wherein the dioxolane compound has the formula

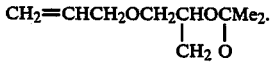

6. A method according to claim 1 further comprising mixing with the dioxolane-substituted organosilicon compound (iv) an amount of an olysis agent comprising a compound selected from the group consisting of hydrolysis compounds and alcoholysis compounds, the conditions of said mixing and the amount of olysis agent being sufficient to convert all of said dioxolane radicals to diol radicals, thereby forming a diol-substituted organosilicon compound containing at least one silicon-bonded diol radical having the formula

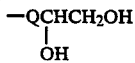

where Q has the stated meaning; all remaining silicon valences of the diol-substituted organosilicon compound being satisfied by radicals free of aliphatic unsaturation selected from the group consisting of monovalent hydrocarbon radicals, monovalent halohydrocarbon radicals, monovalent hydrolyzable radicals, hydroxyl radicals, hydrogen atoms, divalent radicals joining silicon atoms and mixtures thereof.

7. A method according to claim 6 wherein the dioxolane-substituted organosilicon compound is an organosilane having the formula

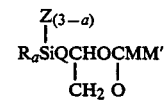

where Z is said monovalent hydrolyzable radical, a has a value of 0, 1, 2 or 3 and R is said monovalent hydrocarbon or halohydrocarbon radical.

8. A method according to claim 7 wherein Z is chlorine, R is Me and each of said dioxolane radicals has the formula

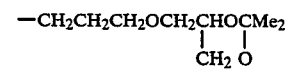

where Me is a methyl radical.

9. A method according to claim 6 wherein the dioxolane-substituted organosilicon compound is an organosiloxane having the formula

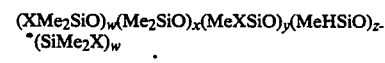

where Me is a methyl radical, X is selected from the group consisting of hydrogen atoms and said monovalent hydrocarbon and halohydrocarbon radicals and dioxolane radicals, x, y and z have average values of 0 or more and, for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded dioxolane radicals per molecule of organosiloxane.

10. A method according to claim 9 wherein each of said dioxolane radicals has the formula

11. A method according to claim 6 further comprising mixing with the diol-substituted organosilicon compound (v) an amount of an acryl compound having the formula

where R'' is H or CH$_3$ and G is selected from the group consisting of halogen, hydroxy, alkoxy and CH$_2$=CR''CO$_2$—, said amount of acryl compound and the conditions of said mixing being sufficient to convert all of said diol radicals to diacrylate radicals, thereby forming a diacrylate-substituted organosilicon compound containing at least one silicon-bonded diacrylate radical having the formula $$-\underset{\underset{O_2CCR''=CH_2}{|}}{Q}CHCH_2O_2CCR''=CH_2,$$

where Q and R" have the stated meanings, all remaining silicon valences of the diacrylate-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms, divalent radicals joining silicon atoms and mixtures thereof.

12. A method according to claim 11 wherein the diol-substituted organosilicon compound is an organosiloxane having the formula (LMe$_2$SiO)$_w$(Me$_2$SiO)$_x$(MeLSiO)$_y$(MeHSiO)$_z$-(SiMe$_2$L)$_w$ where Me is a methyl radical, L is selected from the group consisting of said monovalent hydrocarbon and halohydrocarbon radicals, hydrogen atoms and diol radicals, x, y and z have average values of 0 or more and, for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded diol radicals per molecule of organosiloxane.

13. A method according to claim 12 wherein each of said diol radicals has the formula $$-CH_2CH_2CH_2OCH_2\underset{\underset{OH}{|}}{C}HCH_2OH.$$

14. An organosilicon compound containing at least one silicon-bonded dioxolane radical that is prepared by the method of claim 1.

15. An organosilicon compound containing at least one silicon-bonded diol radical that is prepared by the method of claim 6.

16. An organosilicon compound containing at least one silicon-bonded diacrylate radical that is prepared by the method of claim 11.

17. A dioxolane-substituted organosilicon compound containing at least one silicon-bonded dioxolane radical having the formula $$-\underset{\underset{CH_2\ O}{|\quad|}}{Q}CHOCMM'$$

where Q is a divalent organic radical which is bonded to the silicon atom by way of a silicon-carbon bond, M is a monovalent hydrocarbon radical free of aliphatic unsaturation containing from 1 to 6 carbon atoms and M' is H or M; all remaining silicon valences of the dioxolane-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms, divalent radicals joining silicon atoms and mixtures thereof.

18. An organosilicon compound according to claim 17 having the formula $$R_a\underset{\underset{CH_2\ O}{|\quad|}}{\overset{\overset{Z_{(3-a)}}{|}}{Si}}QCHOCMM'$$

where Z is said monovalent hydrolyzable radical, a has a value of 0, 1, 2 or 3 and R is said monovalent hydrocarbon or halohydrocarbon radical.

19. An organosilicon compound according to claim 18 wherein Z is chlorine, R is Me and each of said dioxolane radicals has the formula $$-CH_2CH_2CH_2OCH_2\underset{\underset{CH_2\ O}{|\quad|}}{C}HOCMe_2$$

where Me is a methyl radical.

20. An organosilicon compound according to claim 17 having the formula (XMe$_2$SiO)$_w$(Me$_2$SiO)$_x$(MeXSiO)$_y$(MeHSiO)$_z$-(SiMe$_2$X)$_w$ where Me is methyl, X is selected from the group consisting of said monovalent hydrocarbon and halohydrocarbon radicals, hydrogen atoms, and dioxolane radicals, x, y and z have average values of 0 or more and, for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded dioxolane radicals per molecule of organosiloxane.

21. An organosilicon compound according to claim 20 wherein each of said dioxolane radicals has the formula $$-CH_2CH_2CH_2OCH_2\underset{\underset{CH_2\ O}{|\quad|}}{C}HOCMe_2.$$

22. An diol-substituted organosilicon compound containing at least one silicon-bonded diol radical having the formula $$-\underset{\underset{OH}{|}}{Q}CHCH_2OH$$

where Q is a divalent organic radical which is bonded to the silicon atom by way of a silicon-carbon bond; all remaining silicon valences of the diol-substituted organosilicon compound being satisfied by radicals free of aliphatic unsaturation selected from the group consisting of monovalent hydrocarbon radicals, monovalent halohydrocarbon radicals, monovalent hydrolyzable radicals, hydroxyl radicals, hydrogen atoms, divalent radicals joining silicon atoms and mixtures thereof.

23. An organosilicon compound according to claim 22 having the formula (LMe$_2$SiO)$_w$(Me$_2$SiO)$_x$(MeLSiO)$_y$(MeHSiO)$_z$-(SiMe$_2$L)$_w$ where Me is methyl, L is selected from the group consisting of said monovalent hydrocarbon and halohydrocarbon radicals, hydrogen atoms, and diol radicals, x, y and z have average values of 0 or more and for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded diol radicals per molecule of organosiloxane.

24. An organosilicon compound according to claim 23 wherein each of said diol radicals has the formula $$-CH_2CH_2CH_2OCH_2CHCH_2OH.$$
$$\phantom{-CH_2CH_2CH_2OCH_2C}|$$
$$\phantom{-CH_2CH_2CH_2OCH_2CH}OH$$

25. A composition comprising a diacrylate-substituted organosilicon compound containing at least one silicon-bonded diacrylate radical having the formula $$-QCHCH_2O_2CCR''=CH_2$$
$$\phantom{-QCH}|$$
$$\phantom{-Q}O_2CCR''=CH_2$$

where Q is a divalent organic radical which is bonded to the silicon atom by way of a silicon-carbon bond and R″ is H or $CH_3$; all remaining silicon valences of the diacrylate-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms, divalent radicals joining silicon atoms and mixtures thereof.

26. A composition according to claim 25 wherein the organosilicon compound has the formula $$(AMe_2SiO)_w(Me_2SiO)_x(MeASiO)_y(MeHSiO)_z\text{-}(SiMe_2A)_w$$

where Me is the methyl radical, A is selected from the group consisting of said monovalent hydrocarbon and halohydrocarbon radicals, hydrogen atoms, and diacrylate radicals, x, y and z have average values of 0 or more and for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded diacrylate radicals per molecule of organosiloxane.

27. A composition according to claim 26 wherein each of said diacrylate radicals has the formula $$-CH_2CH_2CH_2OCH_2CHCH_2O_2CCH=CH_2.$$
$$\phantom{-CH_2CH_2CH_2OCH_2C}|$$
$$\phantom{-CH_2CH_2CH_2OCH_2CH}O_2CCH=CH_2$$

28. A process comprising applying a composition comprising a diacrylate-substituted organosilicon compound to a substrate and thereafter exposing the applied coating to acrylate-polymerizing radiation until said organosilicon compound has been converted to the solid state, said organosilicon compound contains at least one silicon-bonded diacrylate radical having the formula $$-QCHCH_2O_2CCR''=CH_2$$
$$\phantom{-QCH}|$$
$$\phantom{-Q}O_2CCR''=CH_2$$

where Q is a divalent organic radical which is bonded to the silicon atom by way of a silicon-carbon bond and R″ is H or $CH_3$; all remaining silicon valences of the diacrylate-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms, divalent radicals joining silicon atoms and mixtures thereof.

29. A process according to claim 28 wherein the organosilicon compound has the formula $$(AMe_2SiO)_w(Me_2SiO)_x(MeASiO)_y(MeHSiO)_z\text{-}(SiMe_2A)_w$$

where Me is the methyl radical, A is selected from the group consisting of said monovalent hydrocarbon and halohydrocarbon radicals, hydrogen atoms, and diacrylate radicals, x, y and z have average values of 0 or more and for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded diacrylate radicals per molecule of organosiloxane.

30. A process according to claim 29 wherein each of said diacrylate radicals has the formula $$-CH_2CH_2CH_2OCH_2CHCH_2O_2CCH=CH_2.$$
$$\phantom{-CH_2CH_2CH_2OCH_2C}|$$
$$\phantom{-CH_2CH_2CH_2OCH_2CH}O_2CCH=CH_2$$

* * * * *